US00PP16774P2

(12) United States Plant Patent

Gossett

(10) Patent No.: US PP16,774 P2

(45) Date of Patent: Jul. 4, 2006

(54) *HEUCHERA* PLANT NAMED 'TNHEU041'

(50) Latin Name: *Heuchera hybrida*
Varietal Denomination: TNHEU041

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 68 days.

(21) Appl. No.: 11/089,420

(22) Filed: Mar. 22, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman LLP

(57) ABSTRACT

A new and distinct hybrid of *Heuchera* plant characterized by rust colored new growth, changing to tan and olive green colored leaves with yellow green colored flowers on burgundy flowering stems, a mounding habit, and excellent vigor.

1 Drawing Sheet

Botanical denomination: *Heuchera hybrida.*
Variety designation: 'TNHEU041'.

The present invention relates to a new and distinct cultivar of *Heuchera hybrida* and given the cultivar name of 'TNHEU041'. *Heuchera* is in the family Saxifragaceae. *Heuchera* 'TNHEU041' originated as a cross of *Heuchera* 'Amber Waves', U.S. Plant Pat. No. 13,348, as the seed parent and an unknown pollen parent. Pollen from selected, experimental, proprietary plants was massed and used as the pollen parent.

This new *Heuchera* is distinguished by:

1. Rust colored spring foliage maturing to olive green summer and winter foliage.
2. Small yellow green flowers in a wand type arrangement on dark peduncles.
3. Mounding habit.
4. Excellent vigor.

This new cultivar has been reproduced only by asexual propagation (division and tissue culture). Each of the progeny exhibits identical characteristics to the original plant. Asexual propagation by division and tissue culture using standard microprogation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photos show two examples of the foliage of a one-year old plant of *Heuchera* 'TNHEU041' growing in one gallon containers in the shade house in Canby, Oreg.

DETAILED PLANT DESCRIPTION

Figure 1:
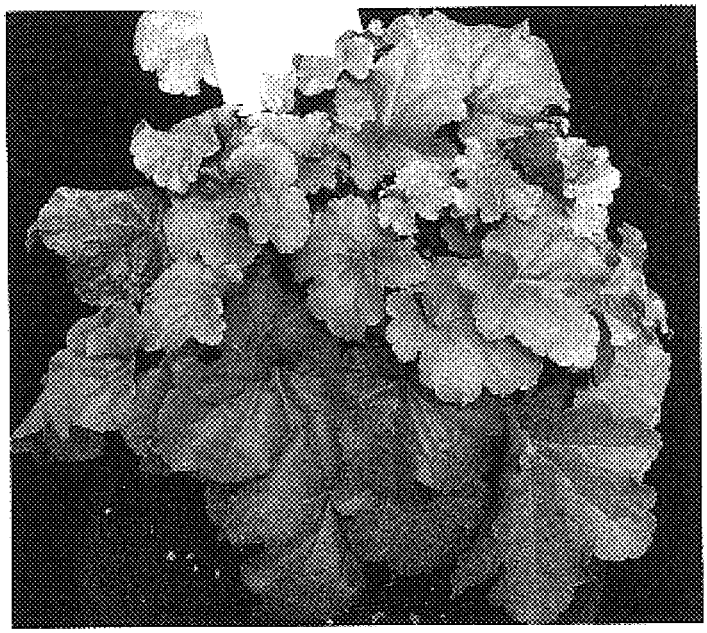
FIG. 1 was taken in May and FIG. 2 was taken in September.
Figure 2:
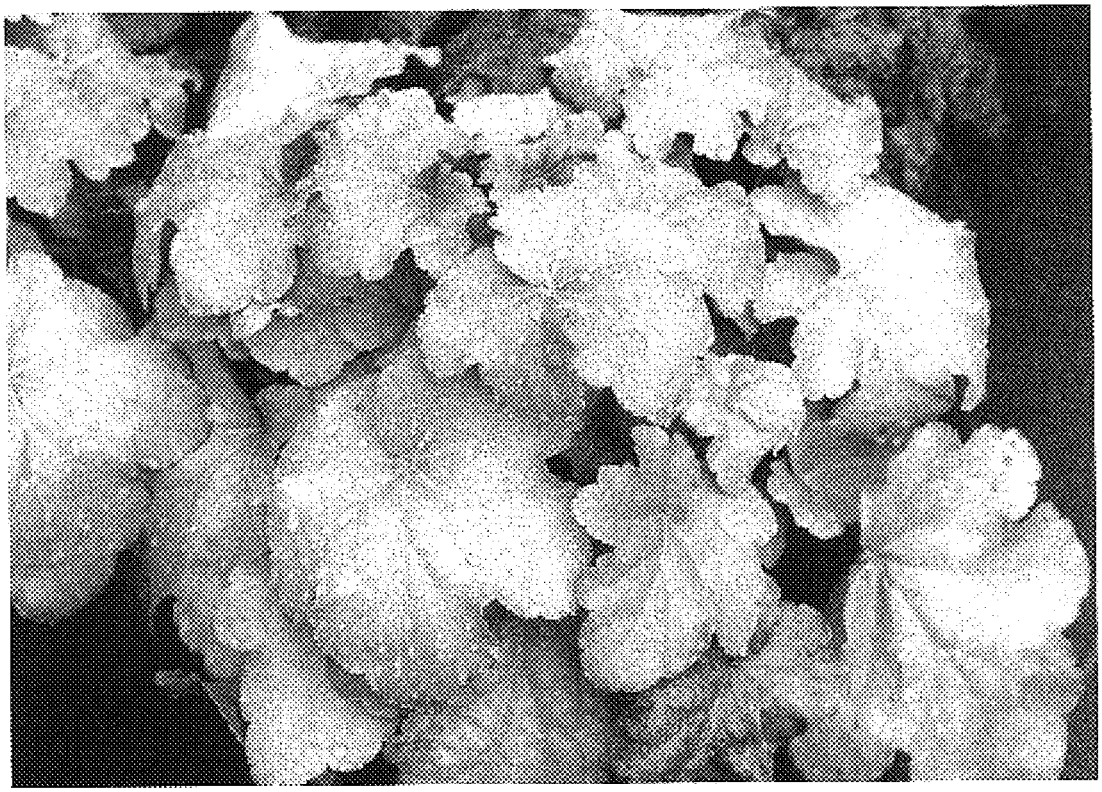

The following is a detailed description of the new *Heuchera* cultivar based on observations taken in June of a three-year-old specimen grown in the ground in an open air shade house with 50% shade cover and added irrigation in the summer months in Canby Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical denomination: *Heuchera hybrida.*
Variety designation 'TNHEU041'.
Parentage: *Heuchera* 'Amber Waves' (seed parent)× unknown (pollen parent).

Plant:
- *Form.*—Basal rosette, herbaceous perennial.
- *Hardiness.*—USDA Zone 4 to 9.
- *Size.*—30 cm tall from the ground to the top of the foliage and 55 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate.
- *Lobing/division.*—5 to 7 main lobes, with 1 to 2 shallow secondary lobes.
- *Venation.*—Palmate.
- *Margins.*—Crenate and slightly undulate.
- *Apex.*—Mucronulate.
- *Base.*—Cordate, lobes overlapping at the base.
- *Blade size.*—Grows to 12 cm long and 11 cm wide.
- *Surface texture.*—Glabrous.
- *Appearance.*—Glossy.
- *Texture.*—Leathery.
- *Petiole length.*—Grows to 23 cm.
- *Petiole vestiture.*—Very short glandular hairs.
- *Petiole color.*—Greyed Red 176A.

*Leaf color*.—Spring and new leaves topside — Greyed Orange 175B. These lighten to Greyed Orange 183A on the newest growth to Greyed Orange 172C with areas tinted Yellow Green 152C. Summer, fall topside — Between Yellow Green 148A and 152A with areas of Greyed Yellow 161A and leaf edges Greyed Red 181A. Winter — Exposed leaves turn Greyed Orange 165A to Greyed Orange 164A. Bottom side spring — Red Purple 60A. Bottom side summer, winter — Between Red Purple 60C and Greyed Purple 185C to 183D.

Inflorescence:

*Type*.—Thyrse.

*Number of flowers*.—100 per thyrse.

*Number of thyrse in first flush in spring*.—12.

*Peduncle*.—With 0 to 3 petiolate cauline leaves, ovate to linear, blades grow to 6 cm long and 4.5 cm wide and are incised at base and crenate. Height — 50 cm. Diameter — 3 mm near base. Color — Greyed Purple 187B. Surface texture — Glandular pubescent.

*Pedicel*.—Length — Variable. Surface texture — Glandular. Color — Grey Brown 199A.

*Bloom period*.—June in Canby, Oreg.

Flower bud:

*Size*.—2 mm wide and 3 mm long.

*Description*.—Glandular, ovoid.

*Color*.—Grey Brown 199A at the base and Greyed Yellow 160A at the top.

Flower:

*Type*.—Perfect, zygomorphic.

*Shape*.—Campanulate.

*Size*.—4 mm long and 4 mm wide.

*Petal count*.—5.

*Petal color*.—Greyed Yellow 160C on both sides.

*Petal shape*.—Spatulate with a clawed base, reflexed, acute tip, margin entire.

*Petal size*.—2 mm long.

*Calyx*.—5 lobes, divided ⅓ way to the base, glandular, tip acute, margin entire.

*Calyx size*.—4 mm long and 4 mm wide.

*Calyx and overall flower color*.—Dull yellow on both sides. Greyed Yellow 160B at the lobes and Grey Brown 199A at the base.

*Stamen*.—5 sterile, Greyed Yellow 160B, 2.5 mm long.

*Pistil*.—Greyed Yellow 160B overall, 3 mm long.

*Fragrance*.—None.

*Lastingness*.—Each thyrse blooms for about 2 weeks on the plant.

Fruit:

*Type*.—Two-beaked ovoid capsule.

*Size*.—4 mm deep and 2.5 mm wide.

*Color*.—Brown 200D.

Seed:

*Shape*.—Linear.

*Size*.—2 mm. long.

*Color*.—Black, RHS 202A.

Pest and disease tolerance:

Excellent disease resistance to powdery mildew, the common problem of *Heuchera*. Susceptible to *Heuchera* rust and root weevils.

COMPARISON TO SIMILAR *HEUCHERAS*

Compared to *Heuchera* 'Amber Waves' (U.S. Plant Pat. No. 13,348), *Heuchera* 'TNHEU041' has greater vigor. The foliage of this new cultivar is less ruffled, larger, and more red tinted. The flowers of *Heuchera* 'Amber Waves' are creamy white rather than dull yellow.

Compared to *Heuchera* 'Marmalade' (U.S. Plant Pat. No. 15,945), this cultivar is more compact in habit with leaves that are larger, shinier, less ruffled.

I claim:

1. A new and distinct hybrid of *Heuchera* plant as herein illustrated and described.

* * * * *